United States Patent [19]

Maly et al.

[11] Patent Number: 4,877,742
[45] Date of Patent: Oct. 31, 1989

[54] PREGNANCY TEST WITH EPF

[75] Inventors: Friedrich E. Maly, Bern; Alain L. de Week, Fribourg; David Henderson, Berlin, all of Fed. Rep. of Germany

[73] Assignee: Schering Aktiengesellschaft, Berlin and Bergkamen, Fed. Rep. of Germany

[21] Appl. No.: 8,239

[22] Filed: Jan. 29, 1987

[30] Foreign Application Priority Data

Jan. 30, 1986 [DE] Fed. Rep. of Germany ....... 3603053

[51] Int. Cl.$^4$ ........................................... G01N 33/48
[52] U.S. Cl. .................................... 436/65; 436/510; 435/173
[58] Field of Search ................... 436/65, 35, 172, 135, 436/136, 138, 172, 510, 810; 435/29, 173

[56] References Cited

U.S. PATENT DOCUMENTS

| | | | |
|---|---|---|---|
| 4,139,348 | 2/1979 | Swartz | 436/35 |
| 4,543,339 | 9/1985 | O'Neill | 436/65 |

FOREIGN PATENT DOCUMENTS

865498A 9/1986 World Int. Prop. O. .

OTHER PUBLICATIONS

Tinneberg et al., Immunochemistry 15-1, pp. 195-210, 1985.
Morton et al., "Detection of Early Pregnancy in Sheep by the Rosette Inhibition Test," *J. Reprod. Fert.*, (1979), 56, 75-80.
Morton et al., "The Appearance and Characteristics of Early Pregnancy Factor in the Pig," *J. Reprod. Fert.*, (1983), 69, 437-446.
Nancarrow et al., "The Early Pregnancy Factor of Sheep and Cattle," *J. Reprod. Fert.*, Suppl. 30, (1981), 191-199.
Grant & Hackh's Chemical Dictionary, 5th Ed., 1987.
Adam, W., In Chemical and Biological Generation of Excited States, Academic Press, pp. 115-152, (1982).
Morton, H., Aust. J. Biol. Sci. 37, 393-407, (1984).
Morton, H. et al., Proc. R. Soc. Lond. B. 193, 413-419, (1976).
Chen., C., et al., Ann. N.Y. Acad. Sci. 442, 420-428, (1985).
Volkman, D. J., et al., J. Immunol. 133(6), 3006-3009, (1984).
Rolfe, B. E., et al., Am. J. Reprod. Immunol. 3, 97-100, (1983).
Smart, Y. C., et al., Fertil. Steril. 35, 397-402, (1981).
Morton, H., et al., In Pregnancy Proteins, J. G. Grudzinskas et al., eds., Academic Press; pp. 391-405, (1982).
Cooper, H. L., Meth. Enzymol. 32 633-636 (1974).
Trush, M. A., et al., Meth. Enzymol. 57, 462-494, (1978).
Rolfe, B. et al., J. Immunol. Methods 70, 1-11, (1984).
Clarke, F. and S. Wilson, In Early Pregnancy Factors, F. Ellendorf and E. Koch, eds., Perinatology Press; pp. 165-177, (1985).
Cavanagh, A. C., ibid., pp. 179-189.
Ehrke, M. J. and E. Mihich. In The Reticuloendothelial System, Plenum Press, vol. 8, 309-347, (1980).
Badwey, J. A. and M. L. Karnovsky, Ann. Rev. Biochem. 49, 695-726, (1980).
Pick, E. and Keisari, Y., Cell. Immunol. 59, 301-318, (1981).
Szuro—Sudol, A. and C. F. Nathans, J. Exp. Med. 156, 945-961, (1982).
Bass, D. A. et al., J. Immunol. 30(4), 1910-1917, (1983).
Baehner, R. L., et al., Blood 48, 309—313, (1976).
Fridovich, I. In Free Radicals in Biology, W. A. Pryor, ed., vol. 1, pp. 239-271, (1976).
Klebanoff, S. J., J. Bacteriol. 95, 2131-2138, (1968).
Nilsson, R., et al., Biochem. Biophys. Acta 192, 145-148, (1969).

*Primary Examiner*—Barry S. Richman
*Assistant Examiner*—Lyle A. Alexander
*Attorney, Agent, or Firm*—Millen, White & Zelano

[57] ABSTRACT

A method for the early detection of a pregnancy comprises determination of EPF in the blood or urine or in a biochemical derivative of the blood or urine of pregnant women, by measuring the influence of EPF on the production of electronically excited states or radicals, especially oxygen radicals, or their secondary products, in leukocyte or cell line preparations. The method can also be used to determine gonadal tumors.

16 Claims, No Drawings

PREGNANCY TEST WITH EPF

BACKGROUND OF THE INVENTION

EPF (Early Pregnancy Factor) is a protein that during pregnancy occurs in the blood or urine or in biochemical derivatives of blood or urine of pregnant women. In addition to its presence during pregnancy, EPF also occurs in these fluids when gonadal tumors exist (testicular or ovarian tumors) [Aust. J. Biol. Sci. 37 (1984) 393-407]. [Fertility and Sterility 35 (1981) 397-402]

EPF binds on lymphocytes and can be detected in the rosette inhibition test. The test is based on the fact that EPF intensifies the inhibition of the active rosette formation between lymphocytes and heterologous erythrocytes by antilymphocyte serum [Proc R. Soc. London Ser. B. 193 (1976) 413-149]. In the rosette inhibition test, EPF can be detected in the serum of pregnant women already within 24 hours after conception (union of ovum and sperm) and 2-3 days later also in the urine of these women. In the case of in vitro fertilization a successful embryo transfer is indicated by the occurrence of EPF about 3 days after the transfer (Ann. N.Y. Acad. Sci. 442:420-8, 1985).

Therefore, with the aid of EPF diagnostics, a pregnancy can be detected at a very early moment (1-5 days after conception). However, the rosette inhibition test is labor-and time-consuming; moreover, it is subject to a high error rate. Even a positive pregnancy is often detected only after repeated tests. On the other hand, to rule out a pregnancy, several repetitions of the test are always necessary.

Therefore there is a great interest in a simple and reliable process for early detection of a pregnancy based on the occurrence of EPF.

SUMMARY OF THE INVENTION

Accordingly, it is an object of this invention to provide such a method, inter alia.

Upon further study of the specification and appended claims, further objects and advantages of this invention will become apparent to those skilled in the art.

It has now been found that EPF exerts a measurable influence on the formation of electronically excited states or radicals, especially oxygen radicals and their secondary products, in a leukocyte preparation or in cell lines. If an EPF-containing serum or EPF-containing urine concentrate is incubated with a leukocyte preparation or with a cell line preparation, and the cells are washed and suitably activated to cause the formation of electronically activated states or radicals, especially oxygen radicals, or their secondary products, then the formation of said states or radicals will be different in the presence of EPF than when EPF is absent, and that difference can be measured. In the case of oxygen radical formation, measured, for example, with luminescence, cytochrome C reduction or $H_2O_2$ determination, a change of the radical flux is found in comparison with the controls not treated with EPF. In the case of the controls, the leukocyte or cell line preparation is incubated with serum or urine concentrate or their biochemical derivatives of nonpregnant women. Generically, the electronically activated states refer to excited states of moieties in the preparations wherein electrons are in energy levels above their ground states.

The invention therefore relates to a method for the early detection of a pregnancy, based on the measurement of EPF's existence by determining this influence of EPF on the formation of electronically activated states or radicals, especially oxygen radicals, or their secondary products, in a leukocyte preparation or in cell lines.

The method according to the invention is also suitable for diagnosis of gonadal tumors in male and female humans, when EPF is detected in accordance with the foregoing and, in females, pregnancy is ruled out.

Further the process according to the invention is also suitable for an early determination of a successful embryo transfer after an in vitro fertilization or for detection of fertilization after an artificial insemination, both, of course, being within the definition of pregnancy.

The process according to the invention is also applicable in the veterinary field as well as in human medicine, especially in the case of farm animals, for example, horses, cattle, swine, sheep, etc. For example, the success rate in artificial insemination is disappointingly low in animals and it is very important for the breeder to know early whether an insemination was successful.

Suitable preparations of the preferred embodiment of EPF test medium (A) and alternative embodiments (B) are described in the following.

A Leukocyte preparation can be effected by:

Taking of blood samples from healthy male donors. Anticoagulating them with 1/10 Na citrate 3.8%. Obtaining of mononuclear leukocytes by centrifuging over a one-stage Ficoll-Hypaque gradient (density 1.077). Repeated washing of the mononuclear cells with Hank's Balanced Salt Solution without $Ca^{++}$, $Mg^{++}$ and without phenol red (HBSS). Taking up of the cells in HEPESbuffered (pH 7.4) Minimal Essential Medium with 100 micrograms/ml of bovine serum albumin (BSA-MEM) without phenol red and adjustment to a cell density of $20 \times 10^6$/ml. Placing into Luminometer tubes (3M, Lumacuvettes) 50 microliters (in each tube) of this suspension, corresponding to $1 \times 10^6$ of mononuclear cells/tube, and storing at $+4°$ C. until measurement, a maximum of 8 hours.

B Cell lines

Alternatively, human mononuclear cells from other sources (e.g., alveolar macrophages, peritoneal cells or cells obtained from marrow) or animal mononuclear cells (e.g., mouse peritoneal cells or mouse marrow cultures) or human or animal cell lines can be used, all of which have the capability of forming electronically excited conditions or radicals, especially oxygen radicals or their secondary products (e.g., "Holt" B Cell line, HL60 and various macrophage lines).

The foregoing preparation details and examples of suitable cells are exemplary only. Amounts, values, processing treatments, etc., can all be varied as long as the resultant preparation is capable of functioning in the method of this invention as described herein. For example, human leukocytes may be obtained from female donors, provided hat these are known not to be pregnant. It is possible that leukocytes from other species will respond to human EPF ("Pregnancy Proteins" (ed. Crudzinskas J., Teisner B. and Seppala M) Academic Press 391-405)

Anticoagulation may be effected by use of heparin or EDTA (ethylenediaminetetraacetate) and separation of leukocytes from other blood components achieved by other standard preparative procedures.

The buffers, washing fluids and incubation media for measurement may be replaced by other isotonic, neutrally buffered solutions compatible with functioning of living cells. Such alternatives are discussed, e.g., in Meth. Enzymology 32 (1974) 633 and 57 (1978) 462.

Typically, the number of cells per test sample will be in the range of $10^3$ to $10^7$ when used in conjunction with the EPF-containing preparations discussed below.

Suitable EPF sources include:

Serum, plasma, urine concentrate or biochemical derivatives of these materials from pregnant women or from patients suspected of having gonadal tumors.

Suitable biochemical derivatives include those conventional derivatives which retain the activity of EPF in the original fluid, e.g., extracts, fractions or concentrates of these fluids prepared by ultrafiltration, chromatographic separation, electrophoretic separation or lyophilization (J. Immunol. Methods 70 (1984) 1–11 and "Early Pregnancy Factors" (ed. F. Ellendorff & E. Koch) Perinatology Press, Ithaca, N.Y.).

The corresponding materials from nonpregnant women or mammalian females and before any embryo transfer or insemination are used as controls.

In one useful technique, 100 microliters of serum of a pregnant woman or control serum is pipetted into a sample of $1 \times 10^6$ mononuclear cells in a Luminometer tube and incubated for 30 minutes at 37° C. Afterwards washing with HBSS is performed several times. Finally, the cells are taken up in 500 microliters of HBSS as measuring medium. As above, these are merely preferred conditions. Cell count, sample amount, incubation period, etc. can all be changed. Typically, 5–500 microliters of serum, 5–500 of plasma and 5–500 of urine are suitable. In the case of urine samples, urea must first be removed, e.g., by ultrafiltration or chromatography to prevent damage to the cells. Suitable incubation conditions are 20°–40° C. for 10–60 minutes. Washing and measuring media can also be chosen at will from the many method-compatible media, which typically are isotonic and approximately neutrally buffered (e.g., pH's of 6.8–8.0.)

For detection of EPF activity, the mononuclear cells are stimulated for formation of electronically excited states or free radicals, especially oxygen radicals or their secondary products. This preferably takes place by addition of phorbol myristate acetate (PMA) in an end concentration of 20–30 ng/ml. Alternatively other dosages of PMA or other stimuli (other phorbol esters, ionophores, detergents, fluoride ions, activation by Fc- or complementary receptors) can be used.

"Electronically excited states" mean the formation of components in the cells wherein electrons are in states other than their normal ground states ["The Reticuloendothelial-system" (Ed. Sbarra and Strauss) Plenum Press, N.Y., (1980) Vol. 8, 309 and Annu. Rev. Biochem. 49 (1980) 695].

For the preferred PMA treatment, typical temperatures are 20°–40° C., treatment times 1–200 minutes, pHs 6.8–8.0, concentrations of PMA in the range of 0.1–1000 ng/ml per $1 \times 10^6$ cells of target medium.

Typically the oxygen or other radicals or other stimulated conditions are made visible in the form of photons (luminometry). This can be accomplished by addition of a chemilumigenic substrate to the cell suspension before initiation of the free radical formation. Generally, Lucigenin in a concentration of 1 uM–1 mM, preferably about 0.1–1 mM is used; alternatively other concentrations of Lucigenin can be used. Also luminol or luminol derivatives (isoluminol, ABEI, AHEI. ABEI-H; ABEI=N-(4-aminobutyl)-N-ethyl isoluminol, ABEI-H=N-(4-amino butyl)-N-ethyl isoluminol hemisuccinamide, AHEI=N-(6- aminohexyl)-N-ethyl isoluminol) or fluorescein and its derivatives can be used as chemilumigenic substrate. Measurement of unintensified chemiluminescence is also possible.

Generally, any measurement means can be used which is capable of detecting the presence of the electronically excited states, e.g., free radicals. Other suitable processes for determination of free radical production include:

Measurement of $0.O_2$ production by means of spectrophotometric detection of the reduction of cytochrome C. [Cell. Immunol. 59 (1981), 301–318].

Measurement of $H_2O_2$ production by means of Scopoletin, phenol red or oxidative fluorogenic substrates (DCFH-DA. DCDCFH-DA: 2',7'-dichlorofluorescin diacetate, 5(and-6)-carboxy-2',7'-dichlorofluorescin diacetate). When the last two are used, a cytofluorographic measurement is also possible. Lit.: J. Exp. Med. 156 (1982) 954–961; Cell. Immunol. 59 (1981), 301–318; J. Immunol. 30(4) (1983), 1910–1917.

Light microscopic determination of the percentage of radical-producing cells by means of nitro blue tetrazolium. Lit.: Blood 48 (1976), 308–313.

The formation of electronically excited states or radicals, for a discussion see "Free radicals in Biology" (Ed. Pryor, W. A.) Academic Press, N.Y., Vol. 1 (1976) 239–277 and J. Bacteriol. 95 (1968) 2131–2138, especially oxygen radicals and their secondary products, can also be detected by electron spin resonance spectroscopy, measurement of natural chemiluminescence or energy transfer to fluorescent substrates (fluorimetry). Lit.: Biochem. Biophys. Acta 192 (1969) 145–148; J. Bacteriol. 95 (1968) 2131–2138; "Chemical and biological generation of excited states" (Ed. Adam, C.) Academic Press, N.Y. (1982) 115–152.

Using such measurement systems, EPF causes a measurable change in the formation of electronically excited states or radicals, especially oxygen radicals and their secondary products, when contrasted with the results where no EPF is present.

In certain circumstances, other substances may interfere with the measurement of EPF (see Example in Table 2, Samples from Clinic H). It is likely that this problem can be circumvented by partial purification of the samples (J. Immunol. Methods 70 (1984) 1–11). Since, as discussed above, leukocytes or their derivatives can be stimulated by a variety of agents to produce radicals, definitive correlation with the presence of EPF is most readily demonstrated by comparison of serum with a control serum taken from the same person before conception has occurred.

Using the method of this invention, early pregnancies are detectable by observation of a statistically significant increase in EPF levels over the standard control values. Typically, levels increase by 25–400% in humans. Where EPF levels are increased in males or in females where no pregnancy is found, then the result indicates the presence of a gonadal tumor.

For this invention, it is necessary to utilize a control sample. In the preferred mode, a sample from the same patients will be used where possible; thus, where in vitro fertilization or artificial insemination is involved or where a female plans natural conception in the near future, adequate samples can be taken prior to the planned events. In this case, the levels of electronic excited states or radical formation in the presence of the patient's own control fluid and the leukocyte or cell sample can be obtained and compared with the raised level in the presence of exactly the same components except for the generated EPF. Where this is not possible, e.g., where it might be expected that a male or female has a gonadal tumor, the EPF determination according to this invention can be carried out and compared with average control levels taken over a statistically relevant number of samples. These average values will be routinely determinable and, of course, will vary with the method used to generate the radical or other excited state. For instance, the average control value for the technique utilized in example (a) below is approximately 400–2000 cpm and in example (b) below it is approximately 100–300 cpm (cpm=counts per minute).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE

Detection of EPF in sera on women after embryo transfer (a) Modulation of the chemiluminescence of mononuclear cells by early pregnancy sera The first blood sample was taken 4–10 days before embryo transfer; other blood samples were taken between 5 and 11 days after embryo transfer. The success of the transfer was evaluated by the usual signs of pregnancy (stopping of the period, positive HCG detection with radioimmunoassay).

To the $1 \times 10^6$ mononuclear cells contained per vial was added 100 microliters of serum. The mixture was incubated for 30 minutes at 37° C. Then the cells in the Luminometer vials were washed three times with Hank's Balanced Salt Solution (HBSS). So as not to lose any cells, the washing medium was not decanted but suctioned off to a defined residue volume of 500 microliters so that the serum concentration was under 0.5% after three washings.

After this, 10 microliters of a Lucigenin solution (12 mM in NaCl 0.9%/tris-HCl 0.01 m, pH 7.2) was added per vial and the vials were introduced into the measurement chamber of the Luminometer. After equilibration of the temperature at 37° C. and stabilization of the background chemiluminescence, 12.5 microliters of phorbol myristate acetate (1 microgram/ml in MEM/BSA) was added as stimulus, corresponding to an end dose of 25 ng/ml.

The integral of the chemiluminescence over 45 minutes from addition of the phorbol ester was selected as a measure of the oxygen radical release by the cells thus treated. Since the sera of different patients, independently of a pregnancy, result in great differences in the oxygen radical formation of the mononuclear test cells, the values of a patient "test serum" were expressed in each case in % of the 45-minute integral obtained with the "control serum" of this patient.

The Biolumat LB 9595 (Berthold, Wildbad, FRG) used for measurement of the chemiluminescence allows parallel measurement of 6 samples. Consequently up to 6 serum samples were put together per measurement series. To be able to perform the comparison of the control and test serum of a patient on the most comparable cells possible, "control" and "test serum" of a given patient were studied in the same test batch.

(b) Modulation of the chemiluminescence of a human B lymphocyte line ("HOLT") by early pregnancy sera The "HOLT" cell line, an Epstein-Barr transformed B lymphocytes line (J. Immunol. 133 (1984), 6) 3006) was kept in RPMI 1640 medium with 10% fetal calf serum. Cells were taken from the culture for the chemiluminescence test, washed twice with MEM/BSA and adjusted to a density of $5 \times 10^6$/ml in MEM/BSA. 200 microliters thereof was introduced per Luminometer vial and kept at +4° C. until further use. The further performance of the chemiluminescence test was essentially identical with the procedure with mononuclear cells. The only change consisted in the use of higher doses of the stimulus phorbol myristate acetate (20–40 micrograms/ml).

Table 1 shows the influence of the chemiluminescence of mononuclear cells (MNC) of a healthy male donor by patient sera after embryo transfer from the Clinic U (U).

In women, who became pregnant (C, E, I, J, L, F) the post-transfer values are clearly over 100% of the control value.

In the case of women who did not become pregnant (S, T, U), the post-transfer values are about 100% of the control value.

In only one woman (R) has a false positive value been found.

By daily treatment with HCG doses of 2–10 thousand IU, the differences between a positive and negative course of embryo transfer are blurred (Table 2, samples from Clinic H).

Further, Table 2 shows the different influence of chemiluminescence of mononuclear cells (MNC) and B lymphocyte lines (BLCL). In the case of successful embryo transfer (ET+), with the use of mononuclear cells, an intensification and, with the use of B lymphocyte cell lines, a reduction of the chemiluminescence is observed.

As in the prior art, the method of this invention can be used to detect a pregnancy at a very early stage, e.g., within 24 hours after conception using blood samples or 2–3 days later using urine samples. The method can also reliably be used during later periods, e.g., up to 12–16 weeks after conception.

TABLE 1

| Sample | Transfer on cycle day | Taking blood on cycle day | Relative Chemiluminescence x ± SD | p | (n) | Result |
|---|---|---|---|---|---|---|
| U C | 14 | | | | | |
| C1 | | 10 | | | | |
| C2 | | 24 | 244 ± 151 | 0.05 | (7) | + |
| C3 | | 27 | 203 ± 34 | 0.1 | | |
| U E | 16 | | | | | |
| E1 | | 9 | | | | |
| E2 | | 24 | 126 ± 51 | NS | (7) | + |
| E3 | | 28 | 141 ± 37 | 0.1 | (4) | |
| U I | 17 | | | | | |
| I1 | | 9 | | | | |
| I2 | | 23 | 307 ± 193 | 0.1 | (5) | + |
| U J | 18 | | | | | |
| J1 | | 8 | | | | |

TABLE 1-continued

| Sample | Transfer on cycle day | Taking blood on cycle day | Relative Chemiluminescence x ± SD | p | (n) | Result |
|---|---|---|---|---|---|---|
| J2 | | 23 | 181 ± 68 | 0.05 | (7) | + |
| U L | 16 | | | | | |
| L1 | | 7 | | | | |
| L2 | | 23 | 188 ± 98 | 0.1 | (6) | + |
| U F | 16 | | | | | |
| F1 | | 9 | | | | |
| F2 | | 24 | 340 ± 103 | 0.05 | (4) | + |
| U S | 16 | | | | | |
| S1 | | 8 | | | | |
| S2 | | 24 | 98 ± 80 | NS | (3) | − |
| U T | 18 | | | | | |
| T1 | | 8 | | | | |
| T2 | | 29 | 120 ± 26 | NS | (4) | − |
| U U | 17 | | | | | |
| U1 | | 8 | | | | |
| U2 | | 25 | 102 ± 35 | NS | (3) | − |

NS = Not significant

TABLE 2

Summary of Samples

| | Clinic U | | | | Clinic H | |
|---|---|---|---|---|---|---|
| MNC | $ET^+$ | 215 ± 133 | (n = 35) | (p < 0.001) | $ET^+$ 96.5 ± 42 (n = 40) (NS) | |
| | $ET^-$ | 101 ± 28 | (n = 20) | (NS) | $ET^-$ 90.8 ± 48 (n = 32) (NS) | |
| BLCL (HOLT) | $ET^+$ | 67.1 ± 27 | (n = 22) | (p < 0.001) | $ET^+$ 117 ± 43 (n = 28) (NS) | |
| | $ET^-$ | 81.5 ± 14 | (n = 8) | (NS) | $ET^-$ 102 ± 26 (n = 20) (NS) | |

$ET^+$ = Successful embryo transfer
$ET^-$ = Unsuccessful embryo transfer

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for early detection of a pregnancy in a female mammal, which does not have a gonadal tumor, comprising determining EPF by measuring its effect on the formation of electronically excited states or free radicals by mononuclear cells or a cell line in a test sample of the female mammal's blood or urine wherein said formation is caused by a treatment effective to form said states or radicals, and comparing said effect to the effect on said formation of a control sample comprising corresponding material from at least one nonpregnant female, which does not have a gonadal tumor, of the same mammalian species, wherein a statistically significant difference between the effect of the test sample compared to the effect of the control sample indicates pregnancy.

2. A method of claim 1 wherein the sample from the female tested for EPF is serum, plasma or urine.

3. A method of claim 1, wherein the sample of blood or urine from the female tested for EPF has been treated in a manner designed to concentrate or enrich the EPF present or to remove species which will interfere with said method.

4. A method of claim 1 wherein the female is a human.

5. A method of claim 1 wherein the female is a domestic mammal.

6. A method of claim 1, wherein the female mammal has become pregnant by artificial insemination.

7. A method of claim 1, wherein the female mammal has become pregnant by in vitro fertilization.

8. A method of claim 1 wherein said mononuclear cells are mammalian alveolar macrophages, peritoneal cells or marrow cells and said cell line is the Holt B Cell line, HL-60 or a macrophage line.

9. A method of claim 1 wherein said cell sample is treated with phorbol myristate acetate to effect said formation of active species.

10. A method of claim 1 wherein said cell sample is treated with a phorbol ester, an ionophore, a detergent, fluoride ions or Fc or complementary receptors, to effect said formation of active species.

11. A method of claim 1 wherein said measurement is by luminometry.

12. A method of claim 1 wherein said measurement is by photometric determination of oxygen radicals or $H_2O_2$.

13. A method of claim 1, wherein the control sample is taken from the same mammalian female prior to conception.

14. A method of claim 1, wherein the effect of the control sample is taken to be the average effect calculated over a statistically relevant number of control samples of corresponding material from a group of nonpregnant mammalian females, which does not have a gonadal tumor, of the same species.

15. A method of claim 1 wherein the measurement comprises the determination of a free radical in said leukocyte or cell line sample.

16. A method of claim 15 wherein the presence of oxygen radicals is determined.

* * * * *